United States Patent
Pupke et al.

(10) Patent No.: US 10,376,655 B2
(45) Date of Patent: Aug. 13, 2019

(54) SYRINGE

(75) Inventors: Holger Pupke, Koenigseggwald (DE); Tilman Roedle, Wolfegg (DE)

(73) Assignee: ARZNEIMITTEL GMBH APOTHEKER VETTER & CO. RAVENSBURG, Ravensburg (DE)

(*) Notice: Subject to any disclaimer, the term of this patent is extended or adjusted under 35 U.S.C. 154(b) by 107 days.

(21) Appl. No.: 13/146,163

(22) PCT Filed: Jan. 22, 2010

(86) PCT No.: PCT/EP2010/000357
§ 371 (c)(1),
(2), (4) Date: Jul. 25, 2011

(87) PCT Pub. No.: WO2010/084006
PCT Pub. Date: Jul. 29, 2010

(65) Prior Publication Data
US 2011/0282295 A1 Nov. 17, 2011

(30) Foreign Application Priority Data

Jan. 26, 2009 (DE) .................. 10 2009 007 250

(51) Int. Cl.
*A61M 5/34* (2006.01)
*A61M 5/31* (2006.01)

(52) U.S. Cl.
CPC ............ *A61M 5/344* (2013.01); *A61M 5/347* (2013.01); *A61M 5/3134* (2013.01)

(58) Field of Classification Search
CPC ........ A61M 5/3202; A61M 2005/3118; A61M 5/344; A61M 5/3134; A61M 5/346;
(Continued)

(56) References Cited

U.S. PATENT DOCUMENTS 2,755,801 A 7/1956 Morando
2,764,978 A 10/1956 Everett
(Continued)

FOREIGN PATENT DOCUMENTS

DE 19717033 A1 11/1998
DE 19956543 A1 5/2000
(Continued)

OTHER PUBLICATIONS

English Translation of the International Preliminary Report on Patentability dated Jul. 26, 2011, incorporating the English Translation of the Written Opinion of the ISA for PCT/EP2010/000357, ISA/EP, Rijswijk, NL, dated Mar. 22, 2010.
(Continued)

*Primary Examiner* — Bhisma Mehta
*Assistant Examiner* — Laura C Schell
(74) *Attorney, Agent, or Firm* — Stephen T. Olson; Harness, Dickey & Pierce, P.L.C.

(57) ABSTRACT

A syringe includes a syringe cylinder and a distal end designed as a syringe cone. The distal end comprises a region set back in a radial direction such that an edge extending in the circumferential direction is formed. The edge has a first chamfer, and comprises an attachment piece having a clamping region. Holding forces are introduced from the attachment piece via the clamping region in the region of the syringe set back in a radial direction. The clamping region comprises a distal edge. The the distal edge of the clamping region has a second chamfer.

18 Claims, 8 Drawing Sheets

(58) Field of Classification Search
CPC .......... A61M 2039/1077; A61M 39/20; A61M 39/10–39/12; A61M 5/34–5/348; A61M 2039/1033
USPC .................................................. 604/240, 243
See application file for complete search history.

(56) References Cited

U.S. PATENT DOCUMENTS

| | | | |
|---|---|---|---|
| 3,344,787 A * | 10/1967 | MacLean | A61M 5/3202 411/437 |
| 4,676,530 A * | 6/1987 | Nordgren | A61M 39/10 138/89 |
| 5,462,531 A | 10/1995 | Novacek et al. | |
| 5,540,666 A | 7/1996 | Barta et al. | |
| 5,554,134 A | 9/1996 | Bonnichsen | |
| 5,858,000 A | 1/1999 | Novacek et al. | |
| 5,980,495 A * | 11/1999 | Heinz | A61M 5/3202 128/919 |
| 6,824,531 B1 * | 11/2004 | Zecha, Jr. | A61M 5/3216 604/110 |
| 7,273,235 B2 * | 9/2007 | Coquard | F16L 37/0915 285/308 |
| 2002/0062108 A1 * | 5/2002 | Courteix | A61M 5/3202 604/198 |
| 2002/0115984 A1 * | 8/2002 | Guala | A61M 39/1011 604/533 |
| 2003/0032923 A1 | 2/2003 | Eakins et al. | |
| 2004/0087906 A1 * | 5/2004 | Henderson | A61M 5/3134 604/187 |
| 2006/0047251 A1 | 3/2006 | Bickford Smith | |
| 2006/0106349 A1 * | 5/2006 | Kito | A61M 5/344 604/187 |
| 2007/0100294 A1 * | 5/2007 | Sugita | A61M 5/3129 604/241 |
| 2008/0269690 A1 * | 10/2008 | Felix-Faure | A61M 5/3202 604/192 |

FOREIGN PATENT DOCUMENTS

| | | |
|---|---|---|
| DE | 60119728 A2 | 5/2006 |
| EP | 1192965 B1 | 12/1995 |
| EP | 0716860 B1 | 6/1996 |
| EP | 1061975 81 | 2/2004 |
| EP | 1284766 B1 | 3/2005 |
| EP | 1779882 A2 | 5/2007 |
| JP | 6-63049 A | 9/1994 |
| JP | 7-184999 | 7/1995 |
| JP | 2002-505921 A | 2/2002 |
| JP | 2003024441 A | 1/2003 |
| JP | 2003024441 A * | 1/2003 |
| WO | 99/45985 A1 | 9/1999 |
| WO | WO02055140 A1 | 7/2002 |
| WO | WO 2004/037335 A1 | 5/2004 |
| WO | WO 2009/144583 A1 | 12/2009 |
| WO | WO 2010/140019 A1 | 12/2010 |
| WO | WO 2010/150042 A1 | 12/2010 |

OTHER PUBLICATIONS

International Search Report and Written Opinion of the ISA, ISA/EP, Rijswijk, NL, dated Mar. 22, 2010.
Office Action regarding China Application No. 2011-546690 dated Oct. 29, 2013. Translation provided by Suzuye & Suzuye.
Japanese Office Action in parallel procedure for Japanese Application 2011-546690, dratted Apr. 27, 2015, with English translation thereof.
Office Action regarding Japanese Application No. 2015-016959, dated Feb. 16, 2016. Translation provided by Gleiss & Grosse.

* cited by examiner though both the body of the syringe and the attachment piece may have certain manufacturing tolerances.

SYRINGE

CROSS-REFERENCE TO RELATED APPLICATIONS

This application is a 371 U.S. National Stage of International Application No. PCT/EP2010/000357, filed Jan. 22, 2010. This application claims priority to German Patent Application No. 10 2009 007 250.0, filed Jan. 26, 2009. The disclosures of the above applications are incorporated herein by reference.

FIELD

The invention relates to a syringe.

BACKGROUND

Syringes of the type discussed herein are known in the art. They comprise a syringe cylinder and a distal end following thereto that is designed as a syringe cone. The distal end comprises a region that is set back in a radial direction, and wherein—seen in axial direction—an edge is formed extending in the circumferential direction. Especially if the body of the syringe is comprised of glass, for manufacturing reasons and/or due to the stresses existing inside the material, it is not possible to configure this edge with an acute angle and/or at a right angle. Such an edge therefore comprises a chamfer and/or has—seen in the longitudinal section—the shape of a ramp. The syringe has an attachment piece that comprises a clamping region. When the attachment piece is separated from the syringe, preferably the clamping region has an inside diameter that is smaller than the outside diameter of the region that is set back in a radial direction at the distal end of the syringe. When the attachment piece is placed onto the syringe in such a way that the clamping region engages with the region that is radially set back, there results an expansion of the clamping region in a radial direction in such a way that holding forces are introduced into the radially set-back region of the syringe. The clamping region comprises a distal edge.

Overall, the attachment piece is held to the body of the syringe by two mechanisms: on the one hand, a frictional grip exists between the clamping region and the region of the distal end of the syringe that is set back in a radial direction; on the other hand, the distal edge of the clamping region is able to engage with the edge that is configured on the region of the distal end of the syringe that is set back in a radial direction, thereby creating a form closure. The interaction of these two mechanisms is intended to prevent easy removal of the attachment piece by pulling it off the syringe.

Disadvantageously, in the syringes that are known in the art the holding forces that are created by the frictional grip, on the one hand, and the form closure, on the other hand, are often insufficient to guarantee the safe operation of the syringe. Upon activation or operation of the syringe, forces are introduced into the attachment piece that may result in a disengagement of the clamped connection and ultimately the separation of the attachment piece from the syringe. With regard to the form closure, it is especially problematic that in known systems the distal edge of the clamping region has an acute angle or a right angle, while the edge that is formed in the region that is set back in a radial direction comprises a chamfer or is designed as a ramp. The result is a line-shaped contact between the two edges that does not allow for the build-up of any useful friction forces. To the contrary, it is possible for the edge of the clamping region to slip off the ramp-shaped edge of the set-back region resulting in the attachment piece being relatively easily pulled off the syringe.

It can be further seen that the known syringe bodies have a relatively large length tolerance. The attachment piece is typically placed upon the body of the syringe in a predetermined position during machine production. Depending on the actual length of the individual syringe body, the attachment piece is brought into a position that it is—seen in an axial direction—arranged closer to or at a greater distance from the syringe cylinder. Since the region that is set back in a radial direction is typically not configured as cylindrical but as slightly tapered, and wherein the outside diameter increases from the distal end toward the syringe cylinder, the result is that a greater expansion of the clamping region occurs the closer the attachment piece is disposed relative to the syringe cylinder. This additional expansion results in increased material stress and possibly over-expansion. This may reduce the elastic clamping forces whereby it becomes easier to pull the attachment piece off the syringe.

Known syringes are often subjected to sterilization after the attachment piece has already been placed on the body of the syringe. During this process, temperatures may be reached that are close to the glass transition temperature of the material from which the attachment piece is made. In this temperature range, in the course of the sterilization, irreversible expansion and/or relaxation of the material of the attachment piece may occur, whereby in turn the clamping and/or holding forces are reduced and the attachment piece can be pulled off the syringe more easily. This is problematic especially if, due to the arrangement of the attachment piece, the clamping region is already expanded considerably by being disposed in relative close proximity of the syringe cylinder. This causes an elevated pre-stressing of the material that may result, in connection with the sterilization temperature, in a relaxation of the material, thereby causing the holding forces to decrease especially.

SUMMARY

The object of the invention therefore envisions providing a syringe with stronger holding forces that secure the attachment piece on the body of the syringe in order to avoid the disadvantages referred to above.

The object is achieved by a syringe with a distal edge of a clamping region having a chamfer. The chamfer engages with the chamfer that is configured at the edge of the region that is set back in a radial direction, whereby the contact at this location is not a line contact but a surface contact. This way, the frictional forces in this region are increased resulting in a greater holding force. Consequently, a higher force must be applied in order to pull the attachment piece off the body of the syringe than is the case with known syringes.

Also preferred is a syringe on which the chamfer on the region that is set back at the distal end of the syringe is geometrically harmonized with the chamfer on the distal edge of the clamping region of the attachment piece. This allows for optimizing the surface friction that is present in this region, thereby resulting in an additional strengthening of the holding forces.

Especially preferred is a syringe on which the two aforementioned chamfers enclose the same angle with a longitudinal axis of the syringe 1. This way, it is possible to ensure that the chamfers are located adjacent to each other along their total extension.

Further advantageous embodiments are set forth in the sub-claims.

BRIEF DESCRIPTION OF THE DRAWINGS

Subsequently, the invention will be described in further detail using the drawings. Shown are in.

DETAILED DESCRIPTION

Figure 1:
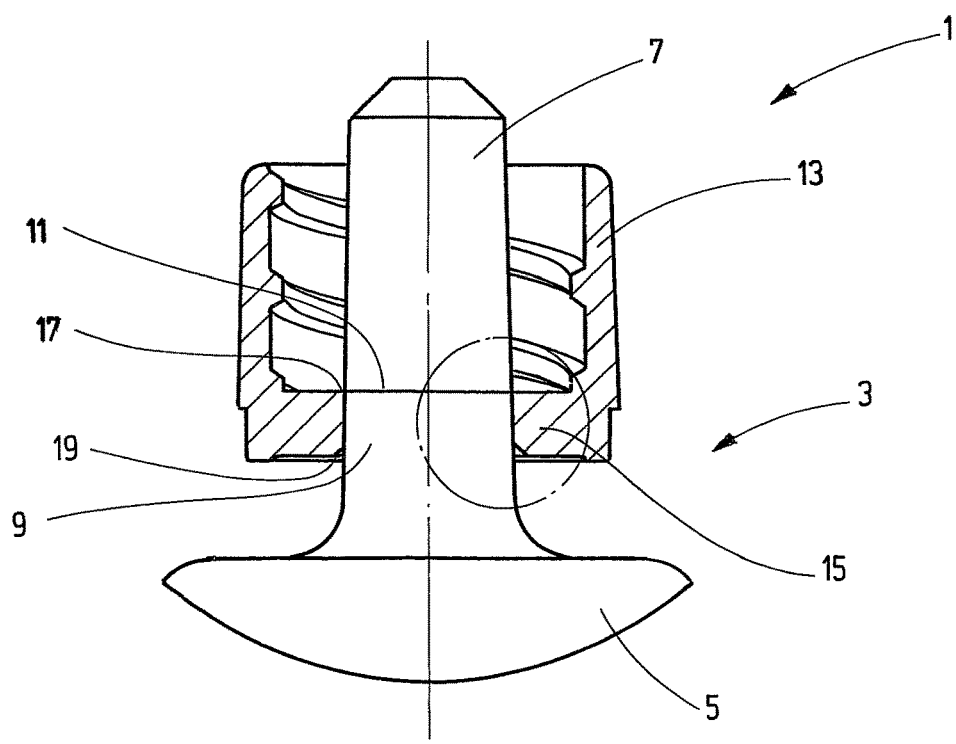
FIG. 1 a sectional view of a first embodiment of a syringe having the attachment piece disposed at a distance from the syringe cylinder.

FIG. 1 shows a sectional view of a first embodiment of the syringe 1. A body of the syringe 3 is only visible in sections. The syringe comprises a syringe cylinder 5 that is followed by a distal end 7 which is designed as a syringe cone. Said end comprises a region 9 that is set back in a radial direction and that can be configured, for example, as a groove or a slot. In the depicted embodiment the distal end 7 is quasi divided in two resulting in a first region that is directed away from the syringe cylinder 5 having a diameter that increases—seen in the direction toward the syringe cylinder 5—whereby this region comprises a tapered external surface, while a second region that is directed toward the syringe cylinder 5 has at the boundary between the two regions a smaller diameter than the first region, thereby constituting the set-back region 9. This set-back region 9 is also configured as somewhat tapered in the shown embodiment, and wherein the diameter—seen in the direction toward the syringe cylinder 5—increases. At the end that is directed toward the syringe cylinder 5 the set-back region 9 transitions directly into the syringe cylinder 5. This is why at this location the diameter increases considerably.

The edge 11 is formed at the boundary between the region 9 that is set back in a radial direction and the first region which is where the diameter—seen in axial direction—changes in a jump-like fashion, and wherein the edge 11 extends around the distal end 7 of the syringe 1.

Edge 11 comprises a chamfer that is not visible in FIG. 1. It is also possible for edge 11 to be configured as a ramp. In particular, if the body of the syringe 3 is comprised of glass it is not possible—seen in a longitudinal section—to envision an edge having an acute or right angle. Edge geometry of this kind would be associated with material stresses that would be too great. An edge 11 with a first chamfer or first surface and/or a ramp therefore results intuitively due to on the manufacturing process of the body of the syringe 3.

The syringe 1 comprises, furthermore, an attachment piece 13. Said attachment piece comprises a clamping region 15 by which the holding forces are introduced into the region 9 of the syringe 1 that is set back in a radial direction. To this end, in a state when the attachment piece 13 is separate from the body of the syringe, the clamping region 15 has an inside diameter that is smaller than the smallest outside diameter of the region 9 that is set back in a radial direction. When the attachment piece 13 is placed onto the body of the syringe and positioned in such a way that the clamping region 15 engages with the region 9 that is set back in a radial direction, there results a dilatation of the clamping region 15, whereby elastic holding forces are introduced in the region 9 that is set back in a radial direction.

Figure 14:
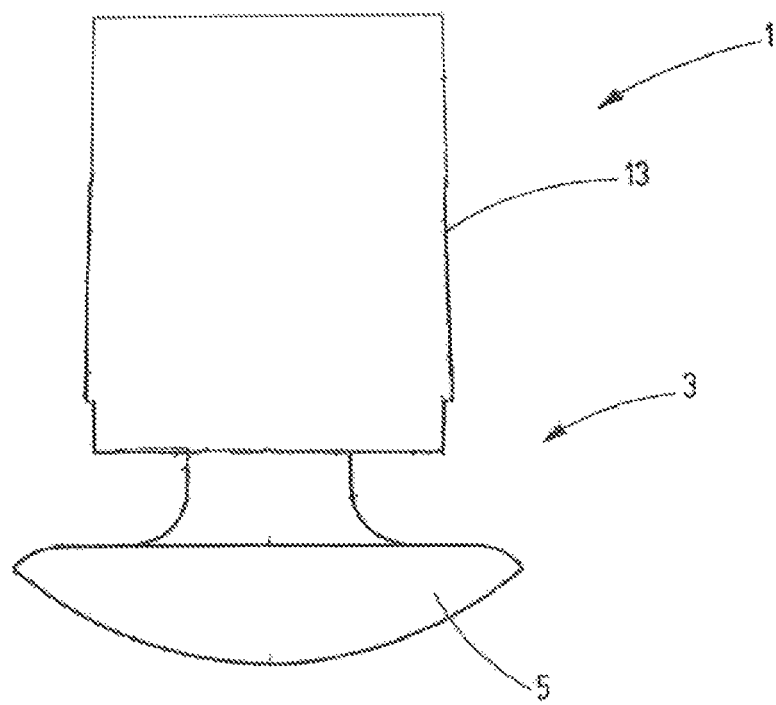
FIG. 14 is a side view of a further embodiment having an attachment piece disposed at a distance from the syringe cylinder, the attachment piece illustrated as a closure element.

In the shown embodiment the attachment piece 13 is configured as a Luer lock. Thus, it is used for providing a leak-proof and secure connection of further injection elements to the syringe 1. In other embodiments the attachment piece can be configured as a closure element (as specifically shown in FIG. 14) or as a connection element. If the attachment piece 13 is configured as a closure element, its purpose is essentially to provide a leak-proof and secure closure of the syringe 1. To this end, it is possible to integrate a guarantee function in the closure element. If the attachment piece 13 is configured as a connection element, it serves as a coupler of the syringe 1 with further injection elements or as a vial adapter and/or to provide a coupling connection with a vial adapter. It is not necessarily required that the coupling action is provided in a way of a Luer lock connection element. Instead different connection elements and/or coupling elements can be used in different embodiments. The only essential aspect in this regard is that the attachment piece 13 be held in place on the body of the syringe 3 by a clamping region 15.

The clamping region 15 comprises a distal edge 17 and a proximal edge 19. In known attachment pieces the distal edge 17—seen in a longitudinal section—is configured as having an acute angle or a right angle, whereby in the shown position of the attachment piece 13 on the body of the syringe 3 it is only possible for the distal edge 17 to establish a line-shaped contact with the edge 11 that is configured as chamfered and/or as a ramp.

It is clearly seen that the attachment piece 13 is held on the body of the syringe 3 by two mechanisms. On the one hand, there results a frictional grip between the clamping region 15 and the set-back region 9 in which the clamping region 15 is expanded resulting in elastic holding forces to be introduced into the set-back region 9. On the other hand, there results a form closure in that the distal edge 17 engages with the edge 11 of the region 9 that is set back.

If only a line-shaped contact exists between the distal edge 17 and the edge 11 that is configured as chamfered and/or as a ramp, the holding force is not optimally supported at this location because only minimal frictional forces are present. To the contrary, the edge 17 may even slip off the chamfer or the ramp that is constituted by the edge 11 when forces are introduced into the attachment piece 13 in an axial direction and that are suitable for causing a separation of the attachment piece 13 from the body of the syringe 3. Forces of this kind can occur, in particular, when preparing the syringe 1 for giving an injection, for example, when screwing the connection elements into the Luer lock of the shown embodiment, when emptying the syringe 1 or also when separating the injection elements.

To increase the holding force of the attachment piece 13 on the body of the syringe 3, the distal edge 17 of the damping region 15 comprises a second chamfer or second surface that is not visible in FIG. 1.

Figure 2:
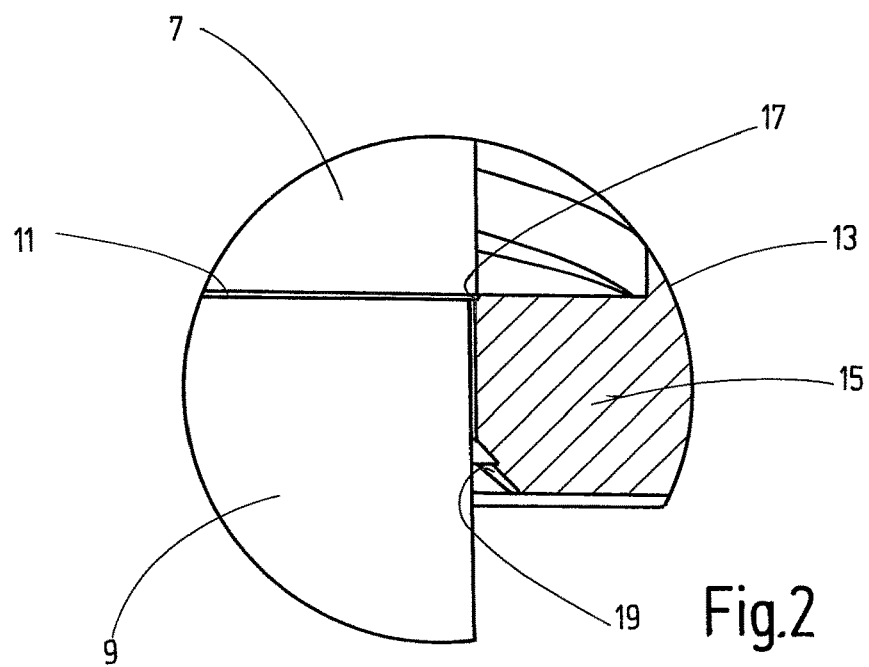
FIG. 2 an enlargement of a section from FIG. 1.

FIG. 2 shows an enlargement of the section that is seen in FIG. 1 and highlighted by a circle. Elements that are identical and that are functionally equal are referenced by the same reference symbols, which is why reference is being made here to the preceding description. It can be seen that the edge 11 comprises a chamfer that it is configured in the present embodiment, in particular, as a ramp. Also visible is the fact that the distal edge 17 of the clamping region 15 comprises a chamfer. Correspondingly, there results surface contact of the chamfers of edges 11, 17, thereby creating increased friction which results in an overall improvement of the holding forces.

Figure 3:
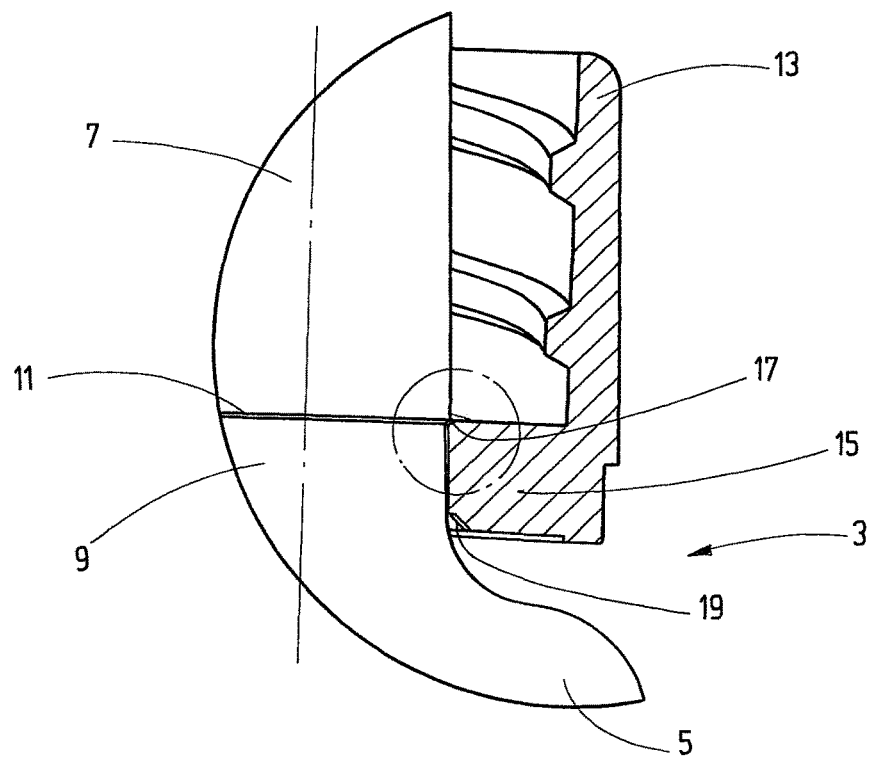
FIG. 3 a further enlargement of a section of the embodiment from FIG. 1.

FIG. 3 shows another enlargement of a sectional view of the embodiment in FIG. 1. Elements that are identical and that are functionally equal are referenced by the same reference symbols, which is why reference is being made here to the preceding description. In this context, the observer sees even more clearly than in FIG. 2 that the edge 11 and the edge 17 both comprise a chamfer allowing them to engage by way of a surface-to-surface contact.

Figure 4:
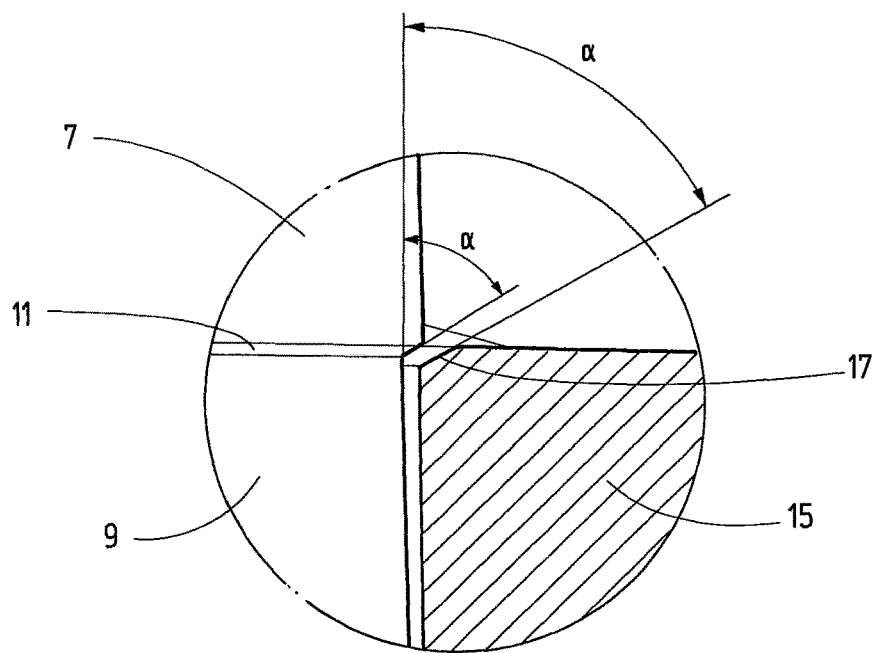
FIG. 4 an enlargement of a section from FIG. 3.

FIG. 4 shows an enlargement of the section that is highlighted by a circle in FIG. 3. Elements that are identical and that are functionally equal are referenced by the same reference symbols, which is why reference is being made here to the preceding description. The clamping region 15 of the attachment piece 13 is drawn here at a certain distance relative to the set-back region 9 of the distal end 7 of the syringe 1 in order to be able to emphasize the characteristics that have been mentioned here even more clearly. In order to further optimize the friction ratio between the chamfered edges 11 and 17 the shown embodiment provides that the edges are geometrically harmonized relative to each other. The edges constitute quasi complementary surfaces, thus providing for a large-surface contact area and thus increased friction.

In particular, in the shown embodiment it is envisioned that the chamfer of edge 11, on the one hand, and the chamfer of edge 17, on the other hand, enclose the same angle α with the longitudinal axis of the syringe 1. The result is an optimal harmonization of the edges 11, 17 with each other in terms of their geometry, thereby creating an especially secure contact action and thus especially high friction.

In the embodiment that is shown in FIGS. 1 to 4 the attachment piece 13 is disposed inside the set-back region 9 in a position that is maximally directed away from the syringe cylinder 5. The result is that the edges 11 and 17 come to lie directly against each other. Since the region that is set back 9 is configured as slightly tapered, the clamping region 15 is in contact with said region at an area having the smallest diameter, and wherein also the dilatation of the clamping region 15 takes—seen along the longitudinal axis of the syringe 1—its minimally possible value.

Figure 5:
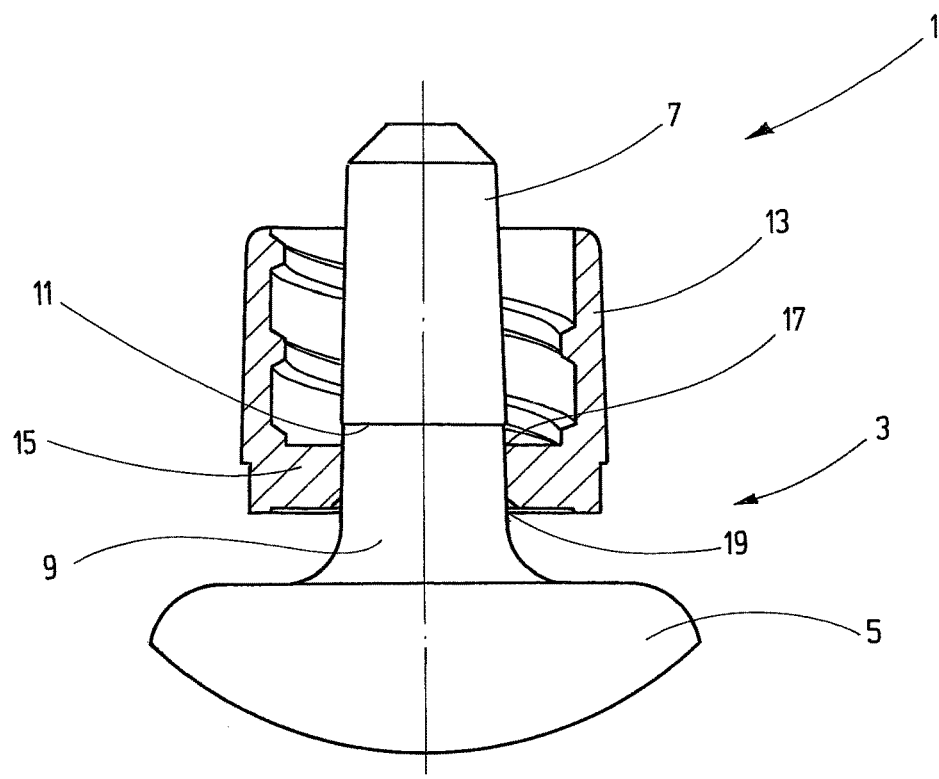
FIG. 5 an embodiment of the syringe having the attachment piece disposed in closer proximity to the syringe cylinder.

FIG. 5, on the other hand, shows an embodiment that has the attachment piece 13 disposed in a position this is—seen along the longitudinal axis of the syringe 1—arranged further toward the cylinder of the syringe 5. Elements that are identical and that are functionally equal are referenced by the same reference symbols, which is why reference is being made here to the preceding description.

The arrangement of the attachment piece 13 within the set-back region 9 is also referred to as the placement position. Different placement positions result from the attachment piece 13 being brought into predetermined positions by the machinery assembling the syringe 1. With regard to its overall length, however, the body of the syringe has a tolerance that is not taken into account during the placement of the attachment piece 13. Correspondingly, for shorter syringes there results a placement position of the attachment piece 13 that is—seen in axial direction—directed away further from the cylinder of the syringe 5 than can be gathered, for example, from FIGS. 1 to 4, while so-called deeper placement positions result for longer syringes in which the attachment piece 13 is disposed in a position that is—seen in axial direction—directed further toward the syringe cylinder 5.

One problematic aspect herein is the taper of the set-back region 9. Since the outside diameter of said region increases in the direction toward the syringe cylinder 5, the clamping region 15 is dilated more in a deep placement position than in a higher-up placement position. In the case of a deep placement position this results in higher material stresses. In the most unfavorable event, the clamping region 15 may thus be overstretched in the deep position resulting in a permanent relaxation of the material and considerably reduced friction and holding forces.

This is particularly problematic in cases when the syringe 1 is sterilized with a pre-positioned attachment piece 13. The temperature ranges that are typically achieved during this process are relatively close to the glass transitioning temperature of the material, which comprises the attachment piece 13 and/or of which the attachment piece consists. Permanent material changes of the attachment piece 13 can be the result of working in these temperature ranges, which causes material relaxation and a considerable decrease of the friction and holding forces.

To avoid this disadvantage, the clamping region in the shown embodiment has an axial extension that is, in relation to half the axial extension of the set-back region 9 at the distal end 7, almost of the same size. It is generally preferred that the axial extension of the clamping region 15 is smaller or of equal size in comparison to half the axial extension of the set-back region 9. Using the total length tolerance of the body of the syringe 3 as basis, it can be seen that even for the deepest conceivable placement positions of the clamping region 15, there occurs no extension into a region that is disposed—seen in axial direction—so closely in relation to the syringe cylinder 5 that would cause concerns with regard to an overexpansion and/or relaxation of the clamping region 15. The axial extension of the clamping region 15 which is reduced according to the invention results in the fact that, independently of the actual length of the body of the syringe 3, only a region of the set-back region 9 is effectively used within the total length tolerance for the clamping action of the attachment piece 13 that is directed away from the syringe cylinder 5. This way, the expansion of the clamping region 15 is limited to acceptable values.

The shown embodiment additionally envisions that the proximal edge 19 of the damping region 15 comprises a third chamfer. Preferably, this chamfer is configured as being relatively wide, thereby contributing to a further reduction of the axial extension of the region that engages in a clamping fashion with the set-back region 9. Thus, in particular with deep placement positions, the chamfer 19 has the effect that the any direct contact of the clamping region 15 in the region of the largest diameter of the set-back region 9 is avoided. Consequently, not only is any over-expansion of the clamping region 15 avoided but, simultaneously, it is achieved that the region of the clamping region that is directed away from the syringe cylinder 5 can make contact safely and securely against the set-back region 9. If the edge 19 were not chamfered, the clamping region 15 would altogether be pre-expanded to the diameter of the set-back region 9 that is in contact with it on the edge 19. Any safe contact of the region that is directed away from the syringe cylinder would no longer apply due to the taper of the set-back region 9.

In the shown embodiment the clamping region 15 comprises a chamfer on the proximal edge 19 as well as a reduced axial extension. But an embodiment in which the clamping region 15 comprises a reduced axial extension while the edge 19 does not comprise a chamfer is also conceivable. Also feasible is an embodiment in which the clamping region 15 has an axial extension that is larger than half the axial extension of the set-back region 9, while the proximal edge 19 comprises a chamfer.

Figure 6:
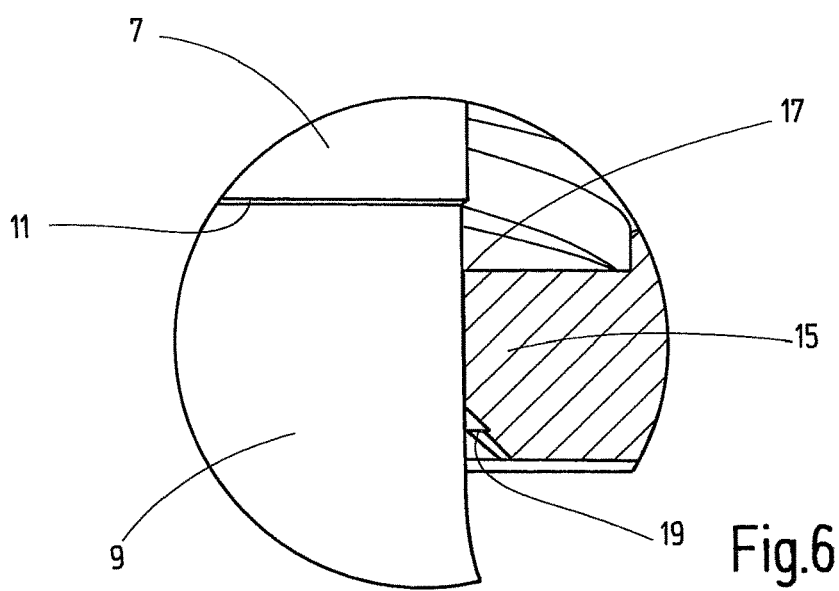
FIG. 6 an enlargement of a section from FIG. 5.

FIG. 6 shows the enlargement of the section from FIG. 5 that is marked therein by a circle. Elements that are identical and that are functionally equal are referenced by the same reference symbols, which is why reference is being made here to the preceding description. In particular, FIG. 6 clearly shows that the proximal edge 19 of the clamping region 15 comprises a chamfer, thereby reducing—seen in axial direction—the effective contact region between the clamping region 15 and the set-back region 9.

The holding forces of the attachment piece 13 on the body of the syringe 3 can be further optimized by providing an advantageous geometrical design of the clamping region 15.

Figure 7:
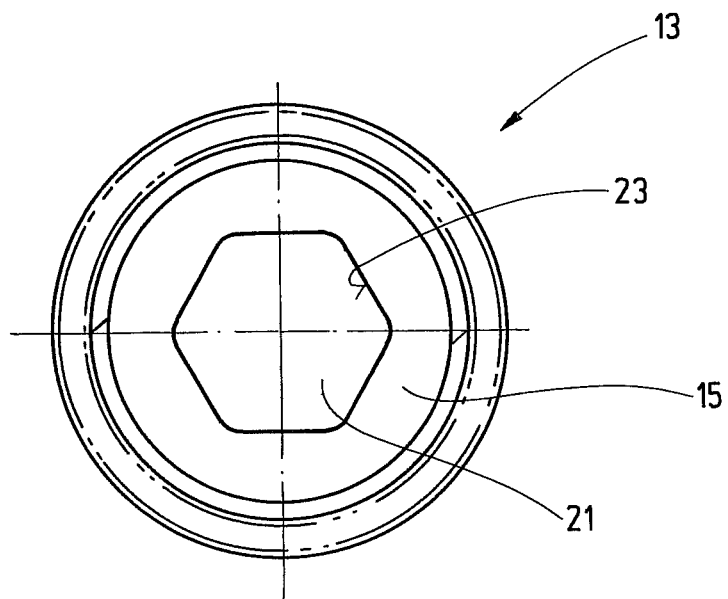
FIGS. 7 to 13 different embodiments of an attachment piece having varying geometries in their clamping regions.

FIGS. 7 to 13 show different views, respectively, of different embodiments of an attachment piece 13 that are at an orthogonal orientation relative to the view shown in FIGS. 1 to 6. The glance of the observer herein is directed along the longitudinal axis of the attachment piece 13. Elements that are identical and that are functionally equal are referenced by the same reference symbols, which is why reference is being made here to the preceding description. FIG. 7 demonstrates that the clamping region 15 comprises a central recess 21 that receives in the assembled state the set-back region 9 of the distal end 7 of the syringe 1. In the embodiment as shown in FIG. 7 the recess 21 has a hexagonal geometry, thereby creating six equivalent contact surfaces one of which is referenced in an exemplary manner by the reference number 23. Thus, in the present instance the clamping region 15 is—seen in a top view—configured hexagonally. It is seen that a hexagonal shape of the clamping region is especially advantageous with regard to the holding forces that are introduced in the region 9 that is set back in a radial direction. In particular, based on the increased holding forces, the hexagonal geometry of the clamping region 15 allows for a reduction of the axial extension of the clamping region 15, whereby said region can be smaller or of equal size in comparison with half the axial extension of the set-back region 9, while the associated loss of friction surface does not have a negative effect on the holding forces.

In the embodiment in FIG. 7, the corners at which two equivalent contact surfaces 23 come to lie adjacent to each other are rounded.

Figure 8:
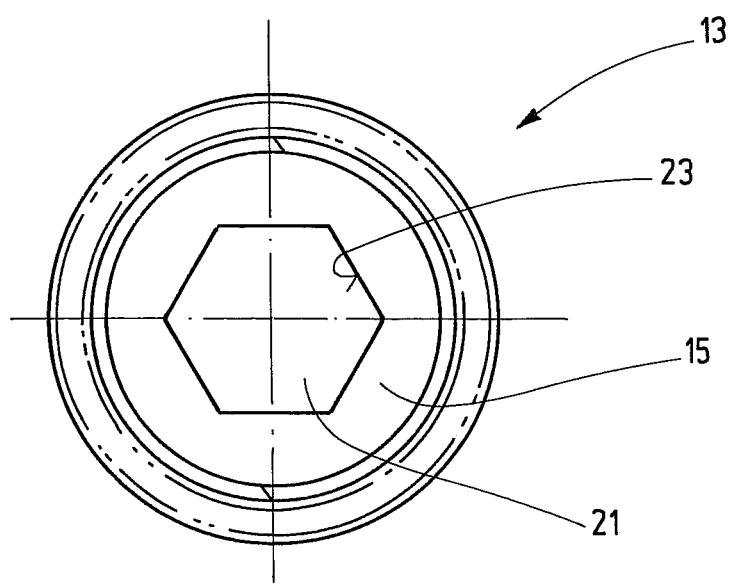

FIG. 8 shows an embodiment that is very similar to the embodiment shown in FIG. 7. A difference is the fact that the corners of the contact surfaces 23 that lie adjacent to each other are not rounded. At any rate, there results a hexagonal clamping region 15 that is—seen in circumferential direction—configured as continuous and comprised six equivalent contact regions 23.

Figure 9:
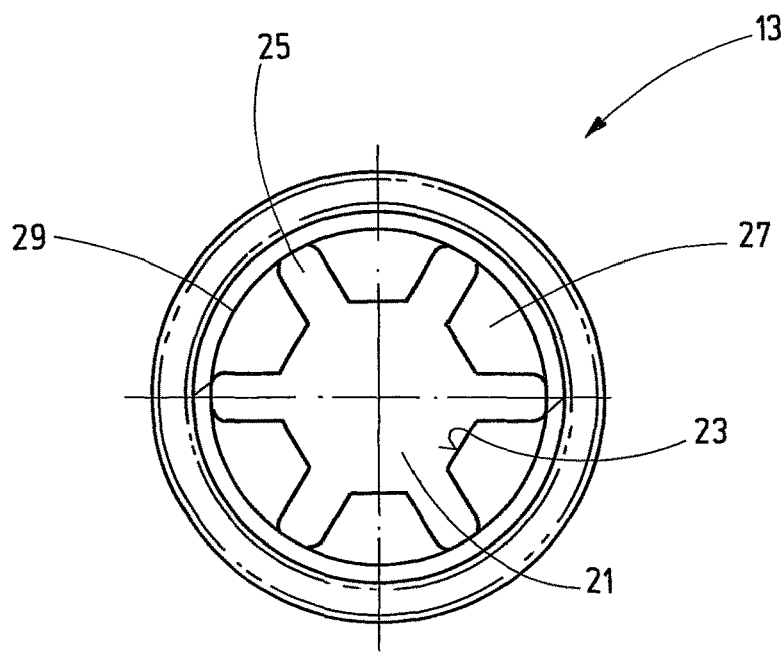

On the other hand, the clamping region 15 of the embodiment shown in FIG. 9—seen in circumferential direction—is not configured as continuous but comprises at least one recess, thereby forming at least one clamping jaw. The concrete embodiment that is shown comprises—seen in circumferential direction—six equivalent recesses 25 that extend essentially radially so that six equivalent clamping jaws 27 are formed. The clamping jaws 27 surround the recess 21 that receives in the assembled state the set-back region 9 of the distal end 7 of the syringe 1. Each of the clamping jaws 27 comprises an equivalent contact region 23 by which holding forces are introduced in the region 9 that is set back in radial direction 9 of the syringe 1. The at least one recess 25 in FIG. 9 has a long-extended form in radial direction and extends from the recess 21 to an outer edge 29 of the clamping region 15.

Figure 10:
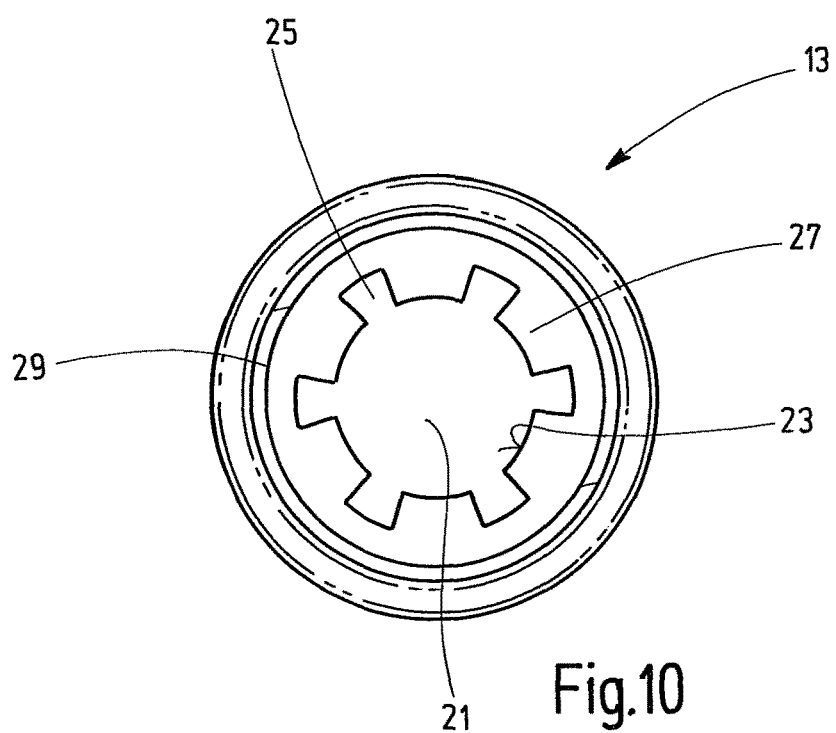

The embodiment according to FIG. 10 also comprises at least one recess 25; in this instance, specifically six equivalent recesses 25. This means, here too, the result is six equivalent clamping jaws 27. In contrast to the embodiment in FIG. 9, however, the recesses 25 do not extend in radial direction from the recess 21 all the way to the outer edge 29 of the clamping region 15 but only to about half of this distance. The clamping region 15 thus comprises—seen in circumferential direction—a continuous area that—seen in radial direction—is directed toward the outer periphery 29. By varying the radial extension of the at least one recess 25 it is possible to adjust the springy elasticity of the individual clamping jaws 27. If the recesses 25 extend—as shown in FIG. 9—over the entire radial expansion of the clamping region 15, the clamping jaws 27 demonstrate high springy elasticity. The less the distance that the recesses 25 extend away from the recess 21 in the direction of the outer periphery 29 of the clamping region 15, the lower is the springy elasticity of the individual clamping jaws 27. This way, using a variation of the radial extension of the recesses 25, it is also possible to achieve a change of the holding forces that are introduced in the set-back region 9. The holding forces can also be pre-determined by the width of the recesses 25: the wider the recesses, the more the holding forces decrease. It is also possible to specifically select the contour of the recesses, which in the present instance increase from the inside to the outside: the wider the recesses are radially on the outside, the lower the holding forces.

Figure 11:
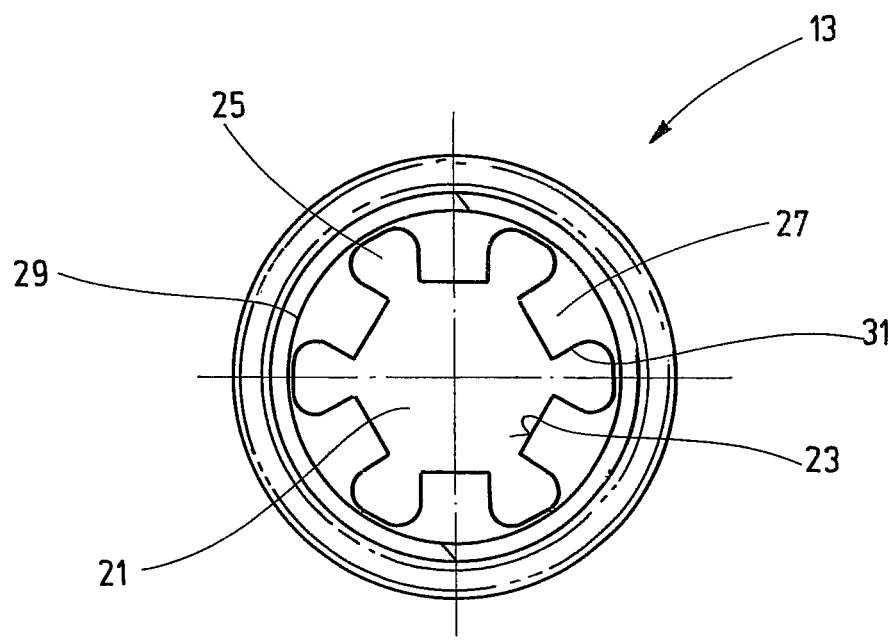

The recesses 25 in FIG. 11—seen in a top view—have a quasi drop-shaped form. This provides the clamping jaws 27 with edges 31 that are positioned perpendicularly relative to the contact surfaces 23. In the outer area of the clamping region 15 this results in an—seen in circumferential direction—increased distance between individual clamping jaws 27. In this embodiment as well, the radial extension of the recesses 25 does not reach completely to the outer periphery 29. The springy elasticity of the clamping jaws 27 can be varied by an interaction of the shape of the recess 25, as seen in a top view, and its radial extension. If the recesses 25—as presently shown—are configured, for example, as drop-shaped, and wherein this results—seen in circumferential direction—in an enlarged distance of the individual clamping jaws 27 relative to each other, the consequence is an increased springy elasticity of the clamping jaws 27. The shape and radial extension of the recesses 25 can thus be adjusted with each other in order to achieve a desired springy elasticity of the clamping jaws 27, and thereby a desired value of the holding forces that are introduced in the set-back region 9.

Figure 12:
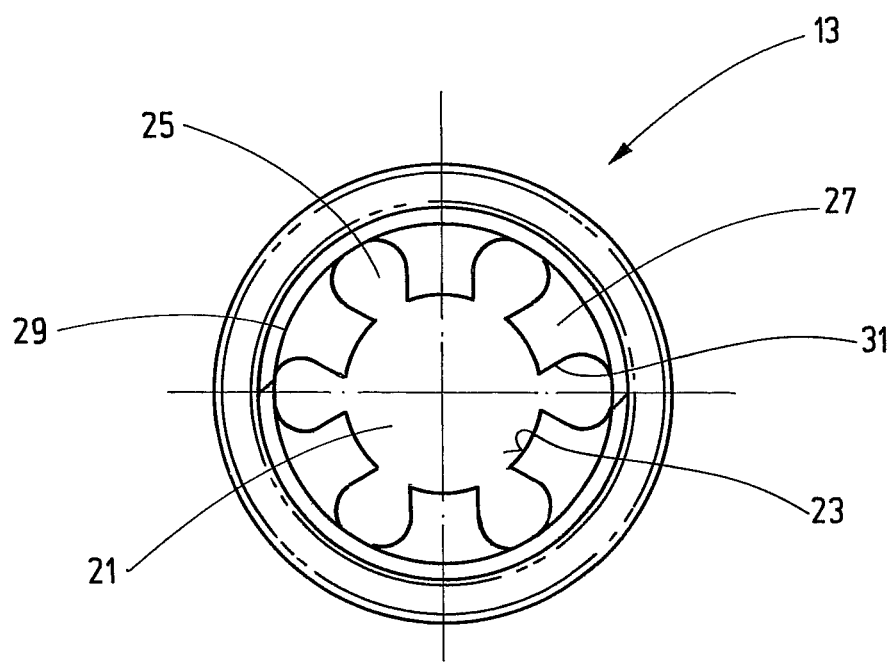

In FIG. 12 the recesses 25—shown in a top view—are also configured as drop-shaped. But their radial extension reaches from the recess 21 all the way to the outer periphery 29 of the clamping region 15. But in contrast to the previous embodiments, the contact regions 23 are not configured as flat; instead they are curved resulting in the formation of cylinder section areas. In this way, the recess 21—seen in a top view—is not delimited by a hexagon but by a circle. Preferably, the curvature of the cylinder-section-shaped contact regions 23 follows the curvature of the set-back region 9 resulting in the shown embodiment in an especially large-surface contact between the contact regions 23 and the set-back region 9. This in turn results in stronger holding forces.

Figure 13:
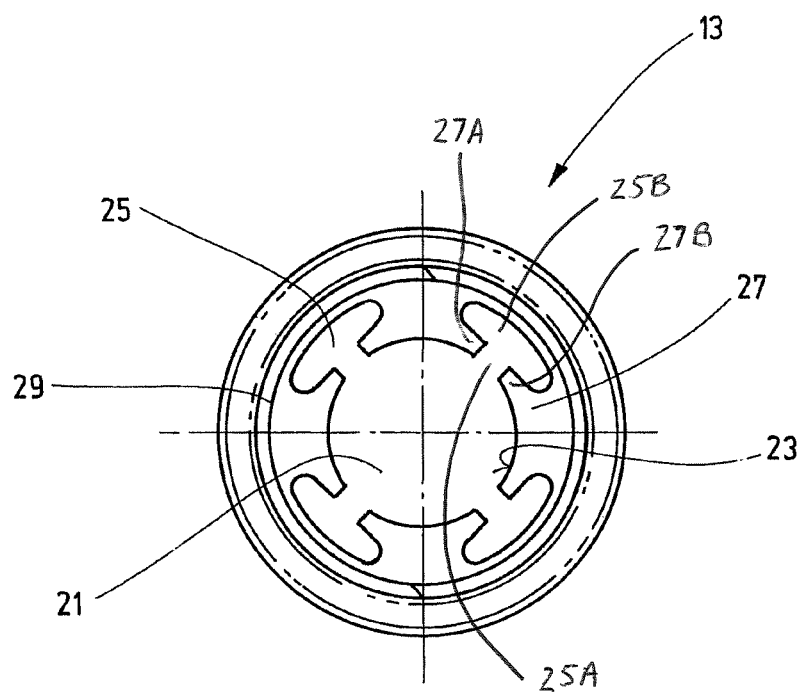

FIG. 13 shows an embodiment of a geometrical configuration of a clamping region that comprises only four recesses 25. The recesses 25 have a-seen in circumferential direction-oblong, oval shape, and wherein they comprise apertures that are disposed symmetrically relative to the short axis of the oval in the direction of the recess 21, thereby constituting four clamping jaws 27. Each jaw 27 includes a first arm 27a extending from a remainder of a respective jaw 27 in a clockwise direction and a second arm 27B extending from the remainder of the respective jaw in a counterclockwise direction. Each recess 25 includes a first portion 25A that extends radially from the recess 21 and a second portion 25B that communicates with the portion 25A. The contact regions 23 in turn are curved in cylinder-section-shape resulting in the recess 21—seen in a top view-being delimited by a circle. The—seen in circumferential direction—oblong, oval shape of the second portion 25B of each of the recesses 25 results in conjunction with the apertures undercuts being formed behind the clamping jaws 27, thereby increasing their elasticity. Simultaneously, the contact regions 23 can be relatively large in this way, whereby a considerable part of the available cylinder area is used for introducing holding forces in the set-back region 9. In this embodiment as well, in the radial direction, the recesses 25 do not extend completely from the recess 21 to the outer periphery 29. But the essential aspect of the shown embodiment is the fact that due to the special geometry of the recesses 25, in which the second portions 25B are oblong in the circumferential direction, a high level of elasticity of the clamping jaws 27 accompanied, simultaneously, by large contact regions 23 is possible.

It is understood that in order to obtain a syringe 1 according to the invention each of the geometries of the clamping regions illustrated in FIGS. 7 to 13 can be combined in any way with the other characteristics that have been described in connection with FIGS. 1 to 6.

Overall, it can be seen that the present invention provides stronger holding forces between the attachment piece 13 and a body of a syringe 3, thereby preventing these elements from becoming inadvertently separated, in particular, during the preparation of an injection. Simultaneously, the present invention avoids the disadvantage that a deep placement position of the attachment piece 13 on the body of the syringe 3 may result in stressing or overexpansion of the clamping region 15, thereby losing the holding forces. Moreover, the disadvantage of a relaxation of material of the attachment piece 13 connected to the body of the syringe 3 during sterilization and accompanied by a loss of the holding forces is avoided.

The invention claimed is:

1. A syringe comprising:
   a syringe cylinder with a distal end configured as a syringe cone, the distal end having a region set back in a radial direction forming an edge that extends in a circumferential direction, the edge defining a first chamfer;
   an attachment piece having a clamping region having a distal edge, the distal edge of the clamping region defining a second chamfer;
   the clamping region of the attachment piece extends proximally from the second chamfer and includes a plurality of recesses and a plurality of jaws defining a plurality of contact regions for engaging the syringe cone, each adjacent jaw spaced from one another in a circumferential direction of the attachment piece by one of the plurality of recesses, wherein the plurality of contact regions form a cylindrically shaped central recess such that the cylindrically shaped central recess extends in a direction parallel to a longitudinal axis of the attachment piece, the clamping region being generally cylindrical;
   a first mechanism for holding the attachment piece to the syringe cylinder defined by a first surface area contact between the first chamfer and the second chamfer; and
   a second mechanism for holding the attachment piece to the syringe cylinder defined by a second surface area contact between the plurality of contact regions and the syringe cylinder,
   wherein each recess includes a first portion that extends radially from the central recess and a second portion communicating with the first portion,
   wherein the second portion of each recess is oblong in shape in the circumferential direction of the attachment piece:
   wherein each jaw of the plurality of jaws has a first arm and a second arm, the first arm of each jaw extending from a remainder of the respective jaw clockwise in the circumferential direction of the attachment piece and the second arm of each jaw extending from the remainder of the respective jaw counterclockwise in the circumferential direction of the attachment piece, and
   wherein each recess is partly defined by the first arm of each respective jaw and by the second arm of each respective adjacent jaw, such that the first portion of each recess is located between the first arm of each respective jaw and the second arm of each respective adjacent jaw, and wherein each adjacent jaw is circumferentially spaced from one another by the first portion of each respective recess such that the clamping region is circumferentially discontinuous when engaging the syringe cone.

2. The syringe according to claim 1, wherein the clamping region of the attachment piece has a smaller diameter than a smallest outside diameter of the region set back in the radial direction.

3. The syringe according to claim 1, wherein the clamping region engages with the region set back in the radial direction to dilate the clamping region and thereby introduce elastic holding forces into the region set back in the radial direction.

4. The syringe according to claim 1, wherein each jaw includes an upper surface and a parallel lower surface, the upper and lower surface of each jaw are oriented generally perpendicular to the longitudinal axis of the attachment piece.

5. A syringe comprising:
   a syringe cylinder with a distal end having a region set back in a radial direction forming a first surface, the first surface extending in a circumferential direction;
   an attachment piece having a clamping region with a distal edge defining a second surface, the first and second surfaces cooperating to define a contact surface therebetween, the clamping region of the attachment piece includes a plurality of recesses and a plurality of jaws, each jaw defining a contact region for engaging the syringe such that the plurality of laws collectively define a plurality of contact regions for engaging the syringe, each adjacent jaw being spaced from one another in a circumferential direction of the attachment piece by a recess,
   wherein each recess includes a first portion and a second portion, the first portion extending radially from a central recess and communicating with the second portion, the second portion being oblong in shape in the circumferential direction of the attachment piece, wherein each jaw of the plurality of jaws has a first arm and a second arm, the first arm of each jaw extending from a remainder of the respective jaw clockwise in the circumferential direction of the attachment piece, and the second arm of each jaw extending from the remainder of the respective jaw counterclockwise in the circumferential direction of the attachment piece, wherein the second portion of each recess is partly defined in an inward radial direction by the first arm of each respective jaw, and further by the second arm of each adjacent jaw, wherein the first arm of each respective jaw and the second arm of each adjacent jaw are spaced from each other in the circumferential direction of the attachment piece by the first portion of the recess, wherein the plurality of contact regions forms the central recess which is cylindrically shaped such that the central recess extends in a direction parallel to a longitudinal axis of the attachment piece, and wherein each adjacent jaw is circumferentially spaced from one another by the first portion of each respective recess such that the clamping region is circumferentially discontinuous when engaging the syringe cylinder, a first mechanism for holding the attachment piece to the syringe cylinder defined by a first surface area contact between the first surface and the second surface; and a second mechanism for holding the attachment piece to the syringe cylinder defined by a second surface area contact between the plurality of contact regions and the syringe cylinder.

6. The syringe according to claim 5, wherein the attachment piece is configured as a closure element.

7. The syringe according to claim 5, wherein the attachment piece is configured as a connection element and the distal end extends completely through the attachment piece.

8. The syringe according to claim 5, wherein the attachment piece is configured as a Luer lock.

9. The syringe according to claim 5, wherein the clamping region of the attachment piece has a smaller diameter than a smallest outside diameter of the region set back in the radial direction.

10. The syringe according to claim 5, wherein the clamping region engages with the region set back in the radial direction to dilate the clamping region and thereby introduce elastic holding forces into the region set back in the radial direction.

11. The syringe according to claim 5, wherein each jaw includes an upper surface and a parallel lower surface, the upper and lower surface of each jaw are oriented generally perpendicular to the longitudinal axis of the attachment piece.

12. A syringe comprising:
a syringe cylinder including a distal end configured as a syringe cone, the distal end including a first region, a second region and a first chamfer therebetween; and
an attachment piece having a clamping region frictionally gripping the first region of the distal end, the clamping region having a distal edge with a second chamfer in a first surface area contact with the first chamfer, the clamping region including a plurality of radially extending jaws and a plurality of recesses, each jaw defining a contact surface such that the plurality of radially extending jaws define a plurality of contact surfaces, each pair of adjacent jaws separated by one of the plurality of recesses, and wherein the clamping region is in a second surface area contact with the first region, wherein the attachment piece is held on to the syringe cylinder through frictional gripping of the first region with the second surface area contact of the clamping region and further held on to the syringe through the first surface area contact between the first and second chamfers; and wherein the plurality of contact surfaces cooperate to form a cylindrically shaped central recess which extends in a direction parallel to a longitudinal axis of the attachment piece, and wherein each recess includes a first portion and a second portion, the first portion of each recess radially extending from the central recess and communicating with the second portion of each recess, the second portion of each recess being oblong in shape in a circumferential direction, wherein each jaw has a first arm and a second arm, the first arm of each law extending from a remainder of the respective jaw clockwise in the circumferential direction, and the second arm of each jaw extending from the remainder of the respective jaw counterclockwise in the circumferential direction, wherein the second portion of each recess is partly defined in an inward radial direction by the first arm of each respective jaw, and further by the second arm of each respective adjacent jaw, wherein the first arm of each jaw and the second arm of each respective adjacent jaw are spaced from each other in the circumferential direction by the first portion of each recess that communicates with the central recess, and wherein each adjacent jaw is circumferentially spaced from one another by the first portion of each respective recess such that the clamping region is circumferentially discontinuous when engaging the syringe cone.

13. The syringe according to claim 12, wherein the attachment piece is configured as a connection element and the distal end extends completely through the attachment piece.

14. The syringe according to claim 12, wherein the attachment piece is configured as a Luer lock.

15. The syringe according to claim 12, wherein the distal end has a region set back in a radial direction forming an edge defining the first chamfer, the clamping region of the attachment piece has a smaller diameter than a smallest outside diameter of the region set back in the radial direction.

16. The syringe according to claim 12, wherein each recess has a first circumferential dimension closer to the central recess and a second, greater circumferential dimension radially spaced from the central recess.

17. The syringe according to claim 12, wherein the attachment piece has an inwardly extending flange at a proximal end thereof, the inwardly extending flange including the plurality of radially extending jaws.

18. The syringe according to claim 12, wherein each jaw includes an upper surface and a parallel lower surface, the upper and lower surface of each jaw are oriented generally perpendicular to the longitudinal axis of the attachment piece.

* * * * *